United States Patent [19]
Foster

[11] Patent Number: 5,989,266
[45] Date of Patent: Nov. 23, 1999

[54] MEDICAL DEVICE INCLUDING BASKET

[76] Inventor: Thomas L. Foster, R. R. 1. Box 755, Poland, Ind. 47868

[21] Appl. No.: 09/028,538

[22] Filed: Feb. 24, 1998

Related U.S. Application Data

[60] Provisional application No. 60/039,448, Feb. 24, 1997.

[51] Int. Cl.$^6$ .................................................. A61B 17/22
[52] U.S. Cl. ........................................... 606/127; 606/114
[58] Field of Search .................................... 606/113, 114, 606/127, 200

[56] References Cited

U.S. PATENT DOCUMENTS

| | | | |
|---|---|---|---|
| 4,425,908 | 1/1984 | Simon | 128/1 |
| 5,057,114 | 10/1991 | Wittich et al. | |
| 5,064,428 | 11/1991 | Cope et al. | |
| 5,133,733 | 7/1992 | Rasmussen et al. | 606/200 |
| 5,330,482 | 7/1994 | Gibbs et al. | 606/113 |
| 5,484,384 | 1/1996 | Fearnot | |

FOREIGN PATENT DOCUMENTS

| | | |
|---|---|---|
| 0123175 | 10/1984 | European Pat. Off. |
| 0160870 | 11/1985 | European Pat. Off. |
| 9216153 | 10/1992 | WIPO |
| 9418888 | 9/1994 | WIPO |
| 9615728 | 5/1996 | WIPO |

*Primary Examiner*—Michael Buiz
*Assistant Examiner*—Jonathan D. Goldberg
*Attorney, Agent, or Firm*—Richard J. Godlewski

[57] ABSTRACT

A minimally invasive, medical device 10 for removing stones, calculus or the like from the renal or biliary systems includes a reversibly collapsible basket 12 and an elongated member 14 for delivering the basket 12 to the location of the stones, calculus or the like. The basket 12 is tipless and atraumatic in use, and includes at least one superelastic wire loop 20 and at least one superelastic wire leg 26, the wire leg 26 preferably being incorporated into a second superelastic wire loop 24. The basket 12 is preferably formed from a shape memory material such as a suitably annealed nitinol alloy. The basket 12 includes means 28 for restricting relative movement of the first wire loop 20 and the wire leg 26 or the second wire loop 24, continuously formed with the first loop 20 and the leg 26 or the second loop 24. The movement restricting means 28 is preferably formed as a first smaller loop 30 in the first loop 20 interlocked with a second smaller loop 32 in the leg 26 or in the second loop 24. The elongated member 14 is preferably a flexible sheath or the like 34 of a length suitable for introduction of the basket 12 into the major and minor renal calyxes. The first loop 20 and the leg 26 or the second loop 24 have longitudinally extending portions 40 and 46 slidably received in the flexible sheath or the like 34. In this way the basket 12 can be retracted into or extended from the elongated member 14. The device 10 is particularly advantageous in being kink-free during use and in possessing a useful diameter significantly smaller than other eggwhip-type retrieval devices.

20 Claims, 4 Drawing Sheets

MEDICAL DEVICE INCLUDING BASKET

CROSS-REFERENCE TO RELATED APPLICATIONS

This application claims priority of provisional application Ser. No. 60/039,448, filed Feb. 24, 1997.

TECHNICAL FIELD

This invention relates generally to medical devices, and more particularly to devices for removing stones, calculi or the like from the body.

BACKGROUND OF THE INVENTION

Various organs and passages in the body are subject to the development of stones, calculi and the like. Gallstones are a common problem in the United States and are the most frequent cause of gallbladder inflammation. Calculi in other parts of the biliary system are also commonplace. Similarly, stones, calculi and the like can develop throughout the renal or urinary system, not only in the ureters and distal to them, but also in the renal tubules and in the major and minor renal calyxes. The calyxes are hollow collecting structures in the kidneys, extending from the renal pelvis, the minor calyxes in particular joining the renal pyramids. For simplicity, the calyxes can be considered as ducts extending from the connecting tubules of the renal nephrons to the ureters.

Minimally invasive surgical procedures have been developed for the removal of stones, calculi and the like from the biliary and urinary systems. Such procedures avoid the performance of invasive, open surgical procedures (such as, for example, the cholecystectomy) and can instead employ percutaneous access, in which stones, calculi and the like are removed through a percutaneously inserted access sheath. Several access routes are suitable, depending upon the specific system and the particular location in the system at which the stones, calculi or the like are found. Without regard to the access route, however, percutaneous extraction is usually based upon the use of either forceps or basket-tipped catheters to engage and remove the stones, calculi and the like.

While forceps enable the quick extraction of stones positioned within ready reach, they are best used in conjunction with endoscopes, to avoid the inadvertent penetration, damage or extraction of intact mucosa. Forceps usually are not suited for the extraction of stones, calculi or the like which are not positioned relatively close to the exits of the biliary and urinary tracts, since forceps cannot negotiate multiple curves in the tracts. It is true that these drawbacks can be partially overcome by the use of basket-tipped catheters which can traverse such winding courses. However, such catheters are often unable to seize impacted stones.

More particularly, basket-tipped catheters can be less than satisfactory in attempting to retrieve very small or flat stones, particularly when the stones lie in large cavities which provide the stones with ample room for displacement. Moreover, most known stone extraction baskets are helically shaped, so that they permit entry of the stone only from the side of the basket. This is typically due to the presence of a discreet tip on the basket, such as a small length of cannula which holds the ends of the wires of the basket together. Thus, a head-on or open-ended approach to the stones is not possible with these "leading tip" retrieval baskets. Moreover, such helically-shaped baskets have a tendency to fold on themselves, rather than to open, when pushed against a wall of a hollow organ. This folding reduces the chance of capturing stones. In addition, the relatively sharp tip of such baskets tends to cause an indentation in the organ wall during capture of the stones, and can lead to damage or injury to the wall of the organ.

There are "open-ended" baskets available in which the wires of the basket form an open loop, and thereby permit a head-on approach to the stones, calculi or the like. The wires of such baskets are formed as plural loops arranged in a manner similar to the loops of a common kitchen tool, the eggwhip, and for that reason baskets of this type are sometimes referred to as eggwhip-type baskets. The wires of such baskets have typically been composed of stainless steel. Stainless steel, however, is often subject to undesirable kinking during use, making it very difficult to push or track the device through the body. Moreover, stainless steel baskets typically do not have a resiliency suitable for more than one stone capture. These drawbacks become particularly acute as the diameter of the device is decreased, as is required for the retrieval of stones located more deeply within the body.

A few devices are known in which the wires of the basket are composed of a superelastic alloy (for example, nitinol), but these particular devices may be subject to their own drawbacks in manufacture or use. For example, they commonly employ suture material to interconnect the most distal ends of the loops to one another. A coating material or adhesive is often applied to the suture material and the underlying section of wire, to fixedly position the suture material and wires relative to one another and prevent the basket loops from sliding at their interconnection. In the absence of such a material or adhesive, the sliding of the loops is allowed to be fairly free, even in the presence of the suture material. No provision is made in these devices for an intermediate degree of restricted sliding or movement of the basket wires with respect to one another. Nor is any provision made, in devices having relatively fixed basket wires, for allowing substantial flexing of the individual wires with respect to one another, without unacceptable kinking. Moreover, the construction of retrieval devices of very small diameter, for example, smaller than about 8 French (8 Fr, or about 2.7 mm), can be problematic, particularly in trying to achieve some sort of securement of the distal ends of the loops to one another.

It should thus be clear that it would be highly desirable to have a minimally invasive device for repeatedly grasping, capturing, retrieving, extracting or removing stones, calculi or the like which was tipless and which was atraumatic during use. It would also be highly desirable to have such a device which possessed superior resistance to kinking during use, and which possessed good pushability and trackability during use. It would further be highly desirable to have such a device which possessed a predetermined, restricted degree of relative movement between the wire loops making up the basket, yet which permitted a very high degree of springiness or flexibility between the pair of wire legs making up each wire loop of the basket. It would further be desirable to eliminate the need for a separate or disparate material to limit relative movement of the wire loops. It would also be highly desirable to have such a device which could possess either an even number or an odd number of wire legs making up the basket. Finally, it would be especially desirable to have such a device in unusually small diameters, from below about 8 Fr (2.7 mm) to even below about 2 Fr (0.7 mm).

SUMMARY OF THE INVENTION

The foregoing problems are solved and a technical advance is achieved in an illustrative minimally invasive, medical retrieval device. Applicant has discovered a way to selectively predetermine and restrict the relative movement of the legs and/or loops of the basket of an eggwhip-type retrieval device, a way which also simultaneously eliminates any tip on the basket and eliminates the need for any disparate material at the distal end of the basket. This not only makes the device highly atraumatic in use, it unexpectedly allows the device to be constructed in very small diameter sizes normally not achieved by basket-type retrieval devices.

More particularly, Applicant has discovered that a specific combination of characteristics is useful for achieving such selective control: making the wires of the legs and/or loops of the basket from a superelastic material; and forming a means for restricting relative movement of the legs and/or loops from the legs and/or loops themselves, the movement restricting means being continuously and kinklessly formed with at least one of the legs and/or loops themselves. The function of the disparate means for fastening or securing the wire loops in prior devices is thus retained while those disparate means are eliminated. Moreover, unlike those prior devices, the present invention allows the legs and/or loops of its basket to be selectively restricted in movement, rather than making relative movement an either-or proposition. The movement restricting means also functions as a torsion spring in such loops, that is, as a torsion spring between the legs making up such loops.

In a first aspect, then, the present invention is directed to a minimally invasive, medical device for grasping, capturing, retrieving, extracting or removing an object from a location within a body, the device comprising a reversibly collapsible basket engageable with the object and an elongated member for delivering the basket to the location of the object; wherein the basket is tipless and atraumatic, and the basket comprises: at least one superelastic wire loop; at least one superelastic wire leg; and means restricting relative movement of the at least one wire loop and the at least one wire leg, the movement restricting means being continuously and kinklessly formed with at least one of (a) the at least one wire loop, and (b) the at least one wire leg.

The movement restricting means preferably comprises a smaller loop formed in either or each of the wire loop and the wire leg. If plural smaller loops are present, they are preferably interlocked. Each smaller loop can depend outwardly from the wire loop or wire leg in which it is formed, although it is preferred that each small loop depends inwardly. It is also preferred, but not necessary, that the basket further comprises at least a second superelastic wire loop incorporating the at least one wire leg. The basket is preferably formed from a shape memory material, such as a Ni—Ti, Cu—Zn—Al or Cu—Al—Ni alloy. It is particularly preferred that the basket is formed from round, flat or triangular annealed nitinol wire.

The elongated member preferably comprises at least one flexible sheath, cannula, tube, catheter or the like so that the basket can be reversibly withdrawn into the flexible sheath or the like. More preferably, the elongated member comprises at least a second protective sheath, cannula, tube, catheter or the like surrounding the at least one flexible sheath or the like. The flexible sheaths or the like can be composed of any of a variety of medical grade, polymeric materials; lubricious materials such as polyethylene and polytetrafluoroethylene are particularly preferred. A handle is preferably connected to the elongated member and the basket for retracting and extending, and for reversibly collapsing, the basket. The at least one loop and the at least one leg preferably comprise longitudinally extending portions slidably received in the elongated member (such as in the at least one sheath or the like) and connected to the handle. The longitudinally extending portions can be secured to one another by one or more collars positioned in the elongated member.

The elongated member can have a very small diameter, preferably as small as about 1.7 Fr to 7 Fr (0.57 mm to 2.3 mm). The diameters of the wire leg and loop (or the wire loops) are then chosen to slidably fit within the elongated member. The appropriate diameters will of course depend upon the number of longitudinally extending portions of the wire leg and loop (or wire loops) received in the elongated member. Typically, the diameter, width or base of the wire leg and loop (or wire loops) will range from about 0.1 mm to about 1.5 mm. For example, in a particularly preferred embodiment of the invention, the elongated member is a sheath of about 3 Fr. (1 mm) outside diameter, and the basket is formed as a pair of wire loops (yielding a total of four longitudinally extending portions) composed of 0.006 in (0.15 mm) nitinol wire.

In a second aspect, the present invention is directed to a minimally invasive, medical device for grasping, capturing, retrieving, extracting or removing stones, calculus or the like from the renal system, the device comprising a reversibly collapsible basket engageable with the object and an elongated member for delivering the basket to the location of the stones, calculus or the like; wherein the basket is tipless and atraumatic, and the basket comprises: a first superelastic wire loop; a second superelastic wire loop; and means restricting relative movement of the first wire loop and the second wire loop, the movement restricting means being continuously and kinklessly formed with the first wire loop and the second wire loop, and being positioned opposite the elongated member; wherein the movement restricting means comprises a first inwardly depending smaller loop formed in the first wire loop and a second inwardly depending smaller loop formed in the second wire loop, interlocked with one another; wherein the elongated member comprises a flexible sheath, cannula, tube or catheter of a length suitable for introduction of the basket into the major and minor renal calyxes; wherein the first wire loop and the second wire loop comprise longitudinally extending portions slidably received in the flexible sheath, cannula, tube or catheter and secured to one another; and wherein the device further comprises a handle connected to the flexible sheath, cannula, tube or catheter and to the longitudinally extending portions of the first wire loop and the second wire loop for withdrawing the basket into the flexible sheath, cannula, tube or catheter and collapsing the basket.

The retrieval device of the present invention is particularly advantageous in that it is minimally invasive, atraumatic and kink-free during use, yet can possess a useful diameter significantly smaller than other eggwhip-type retrieval devices. Because it is kink-free, it is useful for repeatedly grasping, capturing, retrieving, extracting or removing several stones, calculi or the like. The retrieval device of the present invention also possesses good pushability and trackability during use. It provides a predetermined, restricted degree of relative movement between the wire loops making up the basket. It eliminates the need for a separate or disparate material to limit relative movement between those wire loops. The basket of the device can possess any odd or even number of legs or loops. Perhaps most importantly, the retrieval device of the present invention can have an unusually small diameter, from below about 8 Fr (2.7 mm) to even below about 2 Fr (0.7 mm).

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION OF THE PREFERRED EMBODIMENT OF THE PRESENT INVENTION

Figure 1:
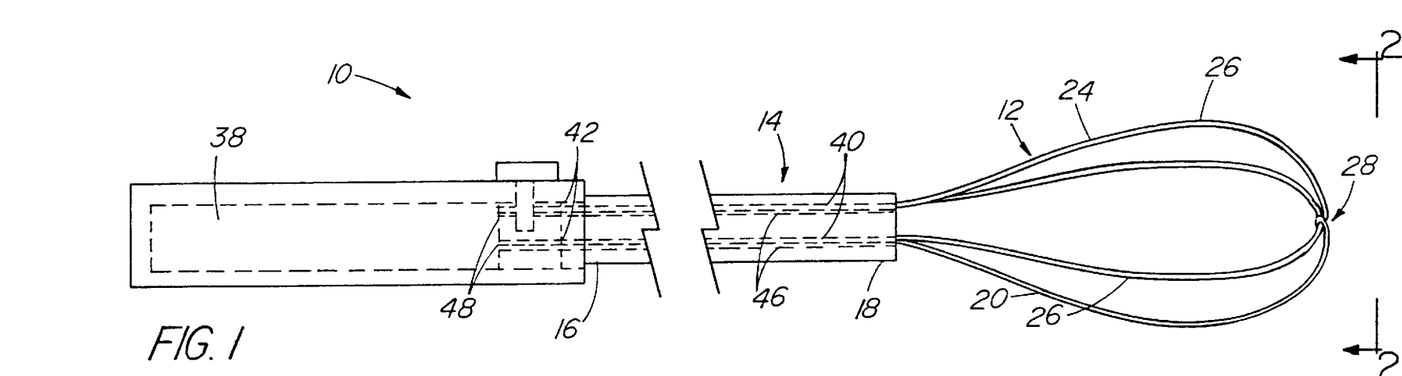
FIG. 1 is a side view of the preferred embodiment of the present invention.

With reference first to FIG. 1, a minimally invasive, medical device for grasping, capturing, retrieving, extracting or removing an object such as a stone, calculus or the like from the body is thereshown, and first comprises a reversibly collapsible basket 12 engageable with the object, and an elongated member 14 for delivering the basket 12 to the location of the object within the body. The basket 12 is preferably formed in a bulbous shape similar to that of a light bulb or a pear. This makes the basket 12 particularly useful for engaging stones, calculi or the like which are located in the bottom portion or a flat area of a body cavity.

The length of the elongated member 14 is selected in view of the location in the body of the object to be engaged. The location of the object also bears upon the diameter selected for the elongated member 14. For example, for the removal of stones, calculi or the like from the major and minor renal calyxes, when the elongated member 14 has an extremely small diameter, for example, such as 1.7 Fr (0.57 mm), 2.0 Fr (0.67 mm), 2.5 Fr (0.83 mm) or 3.0 Fr (1.0 mm), it can conveniently have a length of about 115 to 120 cm. When the elongated member 14 has merely an unusually small diameter, for example, such as about 4.5 Fr (1.5 mm) to 7 Fr (2.3 mm), to perhaps as large as 10 Fr (3.3 mm), the elongated member 14 can conveniently have a length of about 65 to 95 mm.

The basket 12 of the device 10 is characterized in being tipless and atraumatic, and more particularly is characterized in comprising at least one superelastic wire loop 20, at least one superelastic wire leg 26, and a means 28 for selectively predetermining the relative movement of the wire loop 20 and the wire leg 26. The movement restricting means 28 is continuously and kinklessly formed with at least one of, and preferably both of, the wire loop 20 and the wire leg 26. The cross-sectional shape of the wire making up the wire loop 20, the wire leg 26 and the movement restricting means 28 is chosen as convenient. The loop 20, leg 26 and means 28 can be formed from round, flat or triangular wire.

The basket 12, and more particularly the at least one wire loop 20 and the at least one wire leg 26, are preferably formed from or composed of a shape memory material. The best understood shape memory materials are probably the Ni—Ti, Cu—Zn—Al and Cu—Al—Ni metal alloy systems. Particularly preferred for use in the present invention is a Ni—Ti alloy such as nitinol, which exhibits a superelastic property when maintained at a temperature above its transformation temperature. Annealed nitinol is particularly preferred. The transformation temperature of the superelastic basket wire is selected to be below the normal operating temperature of the basket and thereby maintain the basket wire in a superelastic state. In such a state, the superelastic basket wires advantageously return to their original, unstressed shape when any deforming stress is removed from them. The superelastic alloy wire also increasingly resists deformation as the stress load is increased. When nitinol wire is operated below its transformation temperature, heat must be applied to return the alloy wire to its original shape. Advantageously, then, the operating temperature of the superelastic alloy wire of the at least one loop 20, the at least one leg 26 and the movement restricting means 28 of the present invention is maintained above its transformation temperature, so as to resist any significant or appreciable kinking during use, and to return to its original shape without requiring the application of any heat to it.

Figure 9:
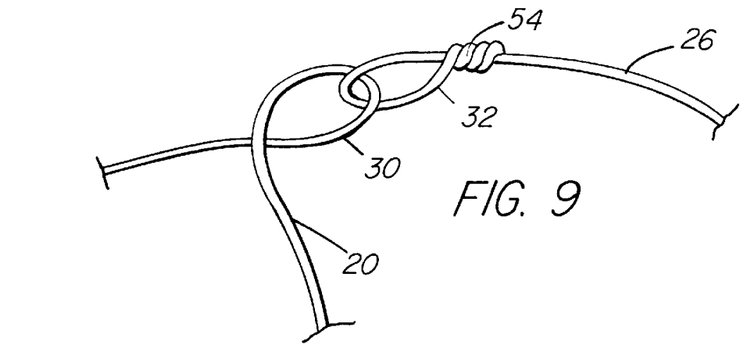
FIG. 9 is a perspective view of a portion of another preferred embodiment of the present invention, similar to the view taken in FIG. 3.
Figure 10:
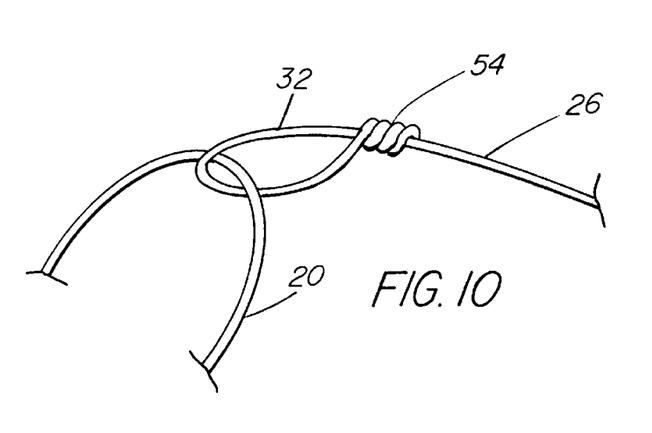
FIG. 10 is a perspective view of still another preferred embodiment of the present invention, similar to the view taken in FIG. 3.

The basket 12 can comprise any desired odd or even number of the at least one superelastic wire loop 20 and the at least one superelastic wire leg 26. Although it is contemplated that the at least one wire leg 26 can stand alone (and embodiments of this type are shown in FIGS. 9 and 10, described in more detail below), it is especially convenient for manufacture and is preferred that the at least one wire leg 26 is incorporated in (that is, it is a part of) at least a second superelastic wire loop 24. The second wire loop 24 can be shaped identically to the first wire loop 20 or can be shaped differently from it.

Figure 2:
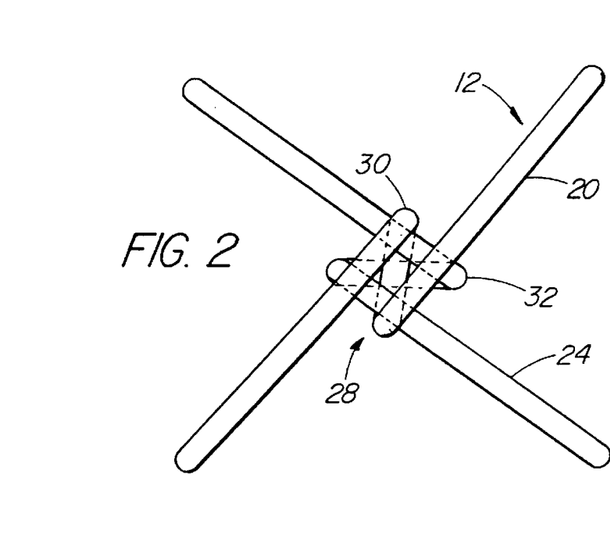
FIG. 2 is an end view taken along line 2—2 of FIG. 1.
Figure 3:
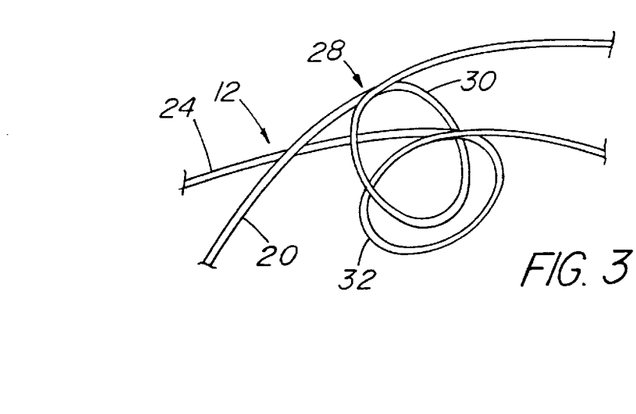
FIG. 3 is a perspective view of a portion of the preferred embodiment of the present invention.
Figure 6:
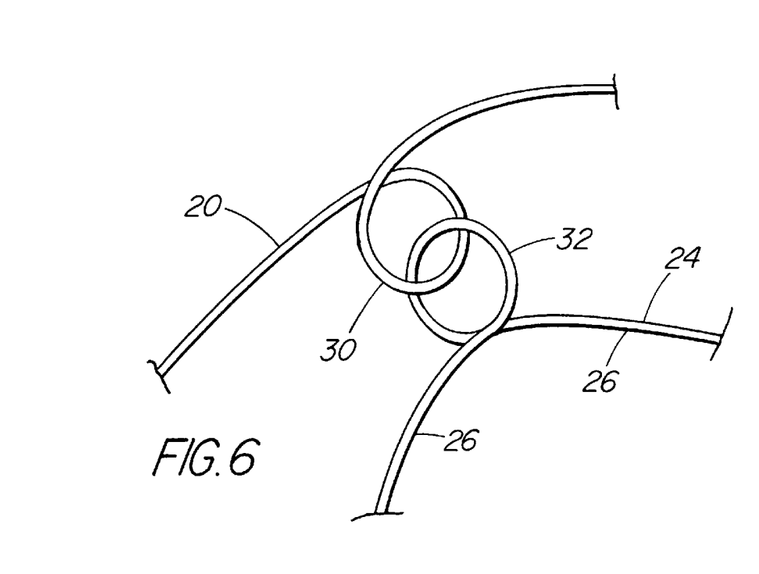
FIG. 6 is a perspective view of a portion of another preferred embodiment of the present invention, similar to the view taken in FIG. 3.
Figure 8:
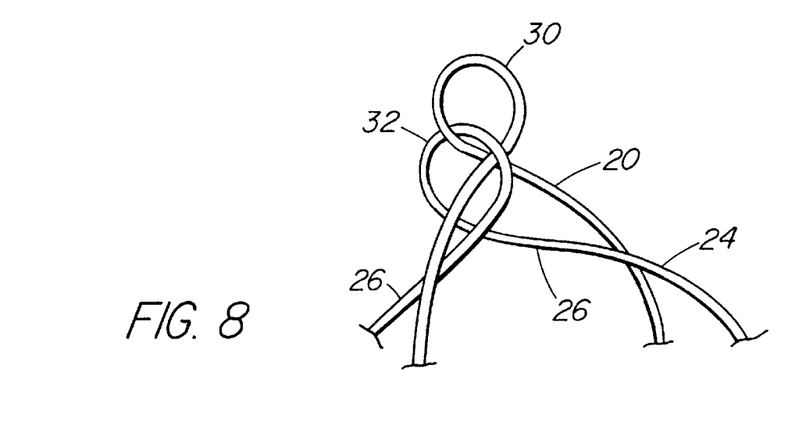
FIG. 8 is a perspective view of a portion of still another preferred embodiment of the present invention, similar to the view taken in FIG. 3.

The movement restricting means 28, as indicated above, is continuously formed with the wire loop 20 and/or the wire leg 26. Conveniently, the movement restricting means 28 comprises one or more smaller loops formed in either or each of the wire loop 20 and the wire leg 26, the smaller loop or loops preferably positioned opposite the elongated member 14. More particularly, the movement restricting means preferably comprises a first smaller loop 30 formed in the first wire loop 20 interlocked with a second smaller loop 32 formed in the wire leg 26. As more clearly shown in FIGS. 2 and 3, the first smaller loop 30 preferably depends inwardly of the wire loop 20, and the second smaller loop 32 depends inwardly of the wire leg 26. Alternatively, as shown in FIG. 8, the first smaller loop 30 can instead depend outwardly from the wire loop 20, and the second smaller loop 32 can depend outwardly from the wire leg 26. Similarly, in another alternative preferred embodiment shown in FIG. 6, one of the first smaller loop 30 and the second smaller loop 32 can depend inwardly, while the other of them can depend outwardly.

Figure 7:
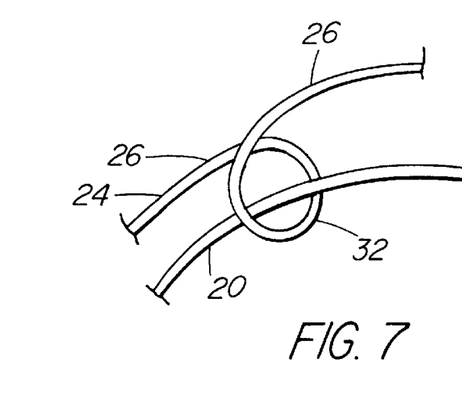
FIG. 7 is a perspective view of a portion of yet another preferred embodiment of the present invention, similar to the view taken in FIG. 3.

In all of these embodiments, the movement restricting means 28 comprises two smaller loops 30 and 32. It should be clear, however, that the present invention also encompasses embodiments in which the movement restricting means 28 comprises only one of the smaller loops 30 and 32, extending either inwardly or outwardly. Such an alternative embodiment is shown in FIG. 7, in which the wire loop 20 extends through the second smaller loop 32 formed in the wire leg 26. Although the wire loop 20 is not interlocked with the second smaller loop 32, movement of the wire loop 20 is still restricted, especially since the wire loop 20 will tend to keep its shape and orientation in use (because it is preferably composed of a shape memory material). An even simpler example of yet another alternative embodiment of the invention is shown in FIG. 10, in which the wire loop 20 extends through a wire leg 26 standing alone. Of course, the wire loop 20 can include its own first smaller loop 30 interlocked with the second smaller loop 32 of the wire leg 26 standing alone (FIG. 9). In the embodiments shown in FIGS. 9 and 10, the second smaller loop 32 is formed by twisting a distal segment 54 of the leg 26 about itself, before the leg 26 is treated to permanently give it its preferred shape. Again, it should be clear from the foregoing that the smaller loops 30 and 32 (the movement restricting means 28) function as torsion springs within the wire loops 20 and 24 in which they are formed.

Figure 4:
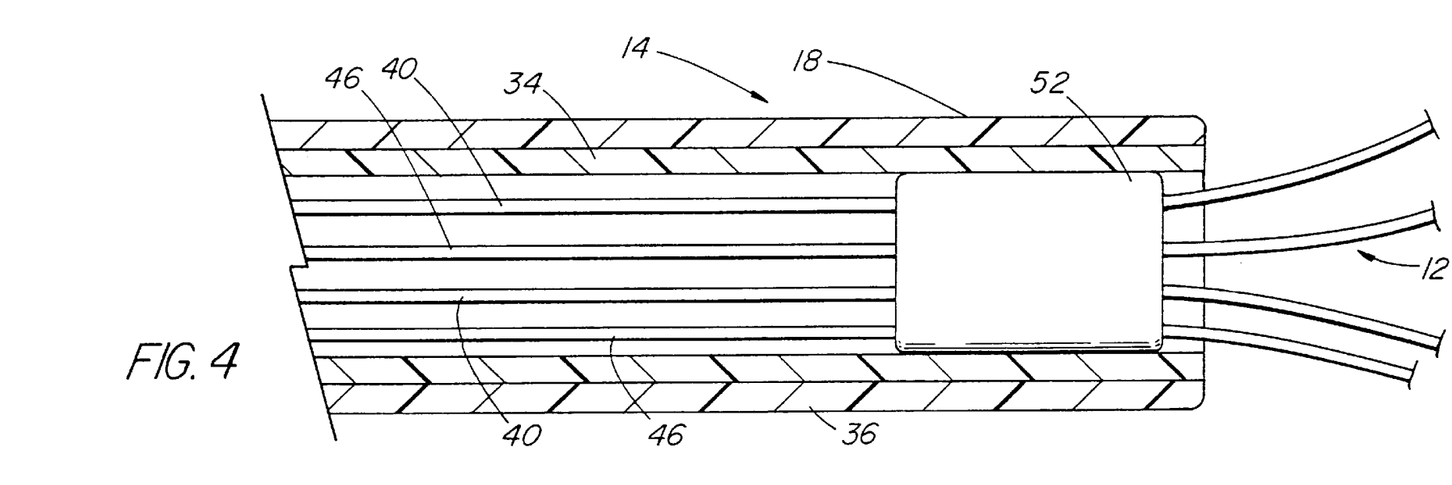
FIG. 4 is a cross-sectional view of another portion of the preferred embodiment of the present invention.
Figure 5:
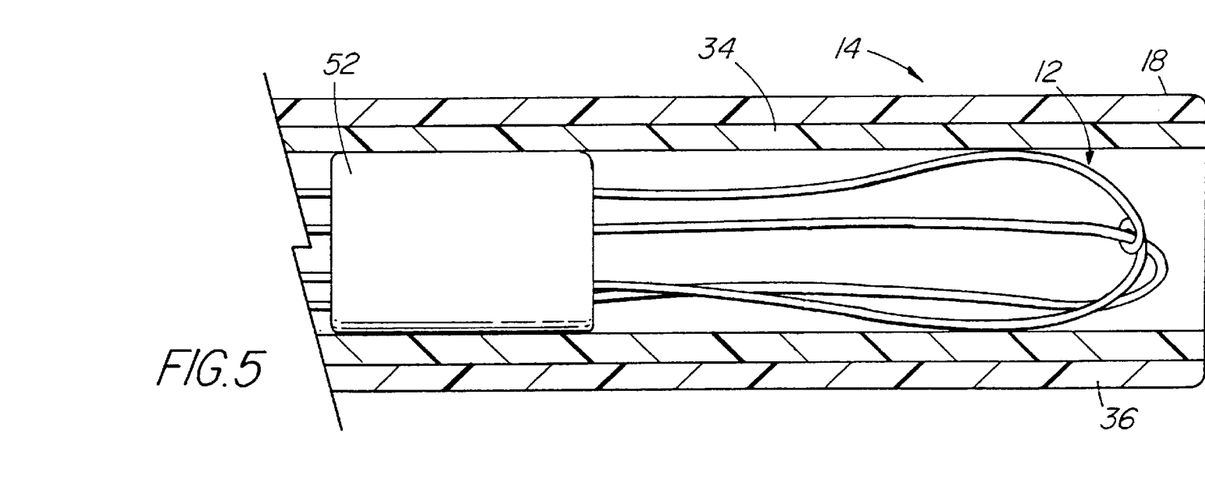
FIG. 5 is a cross-sectional view similar to FIG. 4.

Without regard to the particular structure of the basket 12, it is of course highly preferred that the basket 1 2 is capable of being reversibly collapsible, preferably by being withdrawn into the elongated member 14. Accordingly, it is highly preferred that the elongated member 14 be hollow. More particularly, as shown in FIGS. 4 and 5, the elongated member 14 preferably comprises at least one flexible sheath, cannula, tube, catheter or the like 34, and more preferably further comprises at least a second flexible sheath, cannula, tube, catheter or the like 36 surrounding the first flexible sheath or the like 34.

The purposes of the first and second sheaths or the like 34 and 36 are conventional and should be readily apparent to those skilled in this art. Sheaths, cannulae, tubes, catheters and similar devices are believed to be equivalent for the purposes of the present invention and therefore are all mentioned together. Since they have differences unrelated to the present invention, however, and since those differences may be significant for the performance of one particular retrieval procedure or another, they have not been identified herein by a single generic term.

The basket 12 is slidably received in the distal end 18 of the elongated member 14 to protect the basket 12 from damage before and during its introduction into the body, and to prevent the basket 12 from inadvertently engaging untargeted tissue during introduction. It is therefore preferred that the first flexible sheath 34 or the like be composed of a highly flexible and relatively lubricious material such as polyethylene or polytetrafluoroethylene. The second flexible sheath or the like 36 can be composed of the same highly flexible material, or can be composed of a different material suitable to protect the first flexible sheath 34 before or during its introduction into the body. In its simplest form the second sheath or the like 36 can merely be a protective sleeve adapted to be manually stripped from the device 10 before use. Alternatively, the second sheath or the like 36 can be as complex as an endoscopic sleeve employed to guide the introduction of the device 10 through the body.

The at least one superelastic wire loop 20 and the at least one superelastic wire leg 26 (for example, incorporated into the second wire loop 24) are connected to the elongated member 14 by longitudinally extending portions 40 and 46 on them which are slidably received in the elongated member 14. The longitudinally extending portions 40 and 46 of the first wire loop 20 and the second wire loop 24 are secured to one another by at least one cylindrical collar 52 through which they are received. The at least one collar 52 is preferably composed of stainless steel or another suitable medical grade material, and the longitudinally extending wire portions 40 and 46 are fixed in the collar 52 by a suitable adhesive, such as a cyanoacrylate glue. The wire portions 40 and 46 can also be soldered to the collar 52, but such is probably not preferred, because it is sometimes difficult to solder nitinol to stainless steel.

For clarity, the longitudinally extending portions 40 and 46 have been shown relatively spread apart in FIGS. 4 and 5. However, it should be clear that it is highly desirable that the portions 40 and 46 be packed as closely as possible in the collar 52, to minimize the cross-sectional profile of the device 10.

The basket 12 is collapsed and withdrawn into the elongated member 14 (in particular, into the at least one flexible sheath, cannula, tube, catheter or the like 34) by actuation of a handle 38 connected to the proximal end 16 of the elongated member 14. The longitudinally extending wire portions 40 and 46 of the first wire loop 20 and the second wire loop 24 serve to connect the handle 38 to the basket 12, thereby allowing the handle 38 to selectively push on or draw on the wire portions 40 and 46. Actuation of the handle 38 thus reversibly extends or withdraws the basket 12, and thereby reversibly expands or collapses the basket 12.

Of course, since the first wire loop 20 and the wire leg 26 (for example, incorporated in the second wire loop 24) are joined by the collar 52 at the distal end 18 of the elongated member 14, not all of the longitudinal extending portions 40 and 46 may be necessary to adequately connect the handle 38 to the basket 12. In such a case, one or more of the extending portions 40 and 46 could be eliminated. Care should be taken, however, to ensure that the remaining portions 40 and 46 are sufficiently strong to prevent detachment of the basket 12 from the handle 38 during normal use.

The specific construction of the handle 38 itself is not believed to be critical to the practice of the present invention. Any of an array of conventional handles can be employed, for example, including pin vises, 3ring handles, and unidex handles, among others.

The selection of sintering times for forming the preferred shape for the basket 12 should be well within the skill of anyone in the art, in light of the instant disclosure. By way of non-limiting example, however, suppose that the elongated member 14 has a diameter of 3 Fr (1 mm), so that a nitinol wire diameter of 0.006 in (0.15 mm) is appropriate for the first wire loop 20 and the second wire loop 24. The basket 12 can then conveniently have an overall size of about 1 cm diameter and about 1.3 cm length. The nitinol wire making up the first and second wire loops 20 and 24 can be given its ultimately desired shape memory by forming the nitinol wire into the desired shape cold about a mandrel, and then annealing the wire at about 800° F. (427° C.) for 10 minutes. The time and temperature of annealing will, of course, vary a bit depending upon the diameter and composition of the wire. What must be remembered is that the transformation temperature of the alloy should be below body temperature, and preferably below room temperature, so that the alloy remains superelastic and enjoys good resistance to kinking during deployment in the body.

Suitable annealing of the nitinol or other wire is very important to ensure that the resulting shape memory material is superelastic and resists kinking when manipulated into the very tight radius turns encountered when the basket 12 is withdrawn into the elongated member 14. Without proper annealing, and without the integrally formed movement restricting means 28 (such as the smaller loops 30 and 32, or other elements acting as torsion springs), even conventional nitinol wire would likely kink under such manipulation.

Its structure now having been described in detail, use of the medical device 10 of the present invention should be self-evident to those skilled in this art, and only a cursory summary of such use need be provided here. The handle 38 is first actuated to retract the basket 12 into the elongated member 14, more particularly, into the inner flexible sheath 34, and the inner sheath 34 retracted into the outer flexible sheath 36, if the outer sheath 36 is employed. Under either endoscopic or fluoroscopic control, the elongated member 14 is advanced through the appropriate body passage(s) or any incision(s) made until its distal end 18 lies adjacent to the stone, calculus or the like to be removed. The handle 38 is then actuated to extend the basket 12 from the elongated member 14, preferably, from the first flexible sheath or the like 34, and the device 10 manipulated so as to capture the stone, calculus or the like with the basket 12. The device 10 is then withdrawn from the body, thereby removing the stone, calculus or the like from the body. If more than one stone, calculus or the like is present, the device 10 can be reintroduced into the body to perform additional retrievals. Because the device 10 is tipless, and because the wires making up its basket 12 are superelastic, any risk of inadvertent damage to mucosa or to an organ wall is minimized. Moreover, because the basket 12 comprises superelastic wires, and because the basket 12 is an eggwhip-type basket, the basket 12 advantageously tends to open when pushed against an organ wall, further significantly reducing the risk of wall damage and increasing the probability of capturing the stones, calculi and the like.

It should be clear that the present invention admirably provides a medical device for removing stones, calculi or the like which is advantageous in a variety of ways. The device of the present invention is minimally invasive, tipless and kink-free during use. Because it is kink-free, it is useful for repeatedly grasping, capturing, retrieving or extracting stones, calculi or the like. Because it is tipless, and because its basket is made of superelastic wire, the retrieval device of the present invention is atraumatic in use. It also possesses good pushability and trackability during use. The device further provides a predetermined, restricted degree of relative movement between the wire loops making up the basket, and eliminates the need for a separate or disparate material to limit relative movement between those wire loops. Its basket can possess any odd or even number of legs or loops. Perhaps most significantly, however, the retrieval device of the present invention is advantageous because it can have an unusually small diameter, from below about 8 Fr (2.7 mm) to even below about 2 Fr (0.7 mm).

Any undisclosed or incidental details of the construction or composition of the various elements of the disclosed embodiment of the present invention are not believed to be critical to the achievement of the advantages of the present invention, so long as the elements possess the characteristics needed for them to perform as disclosed. The selection of these and other details of construction are believed to be well within the ability of one of even rudimentary skills in this area, in view of the present disclosure.

Industrial Applicability

The present invention is useful in performing surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A minimally invasive, medical device (10) for grasping, capturing, retrieving, extracting or removing an object from a location within a body, the device (10) comprising a reversibly collapsible basket (12) engageable with the object and an elongated member (14) for delivering the basket (12) to the location of the object; wherein the basket (12) is tipless and atraumatic, and the basket (12) comprises:

at least one superelastic wire loop (20);

at least one superelastic wire leg (26); and means (28) restricting relative movement of the at least one wire loop (20) and the at least one wire leg (26), the movement restricting means (28) being continuously and kinklessly formed with at least one of (a) the at least one wire loop (20), and (b) the at least one wire leg (26).

2. The device (10) according to claim 1, wherein the movement restricting means (28) comprises a first smaller loop (30) formed in the at least one wire loop (20).

3. The device (10) according to claim 2, wherein the first smaller loop (30) depends inwardly of the wire loop (20).

4. The device (10) according to claim 2, wherein the movement restricting means (28) further comprises a second smaller loop (32) formed in the at least one wire leg (26).

5. The device (10) according to claim 4, wherein the second smaller loop (32) depends inwardly of the wire leg (26).

6. The device (10) according to claim 2, wherein the basket (12) further comprises at least a second superelastic wire loop (24) incorporating the at least one wire leg (26).

7. The device (10) according to claim 6, wherein the movement restricting means (28) further comprises a second smaller loop (32) formed in the second wire loop (24).

8. The device (10) according to claim 7, wherein the second smaller loop (32) depends inwardly of the second wire loop (24).

9. The device (10) according to claim 7, wherein the first smaller loop (30) and the second smaller loop (32) are interlocked with one another.

10. The device (10) according to claim 1, wherein the basket (12) includes a nitinol alloy.

11. The device (10) according to claim 1, wherein the elongated member (14) comprises at least one flexible sheath, cannula, tube or catheter (34).

12. The device (10) according to claim 11, wherein the elongated member (14) further comprises at least a second flexible sheath, cannula, tube or catheter (36) surrounding the at least one flexible sheath, cannula, tube or catheter (34).

13. The device (10) according to claim 11, wherein the device (10) further comprises a handle (38) connected to at least the basket (12) for withdrawing the basket (12) into the at least one flexible sheath, cannula, tube or catheter (34).

14. The device (10) according to claim 1, wherein the device (10) further comprises a handle (38) connected to at least the basket (12) for reversibly collapsing the basket (12).

15. The device (10) according to claim 1, wherein the elongated member (14) is about 1.7 Fr to 7 Fr (0.57 mm to 2.3 mm) in diameter.

16. The device (10) according to claim 1, wherein the at least one wire loop (20) and the at least one wire leg (26) are formed from round, flat or triangular wire.

17. The device (10) according to claim 1, wherein the at least one loop (20) and the at least one leg (26) further comprise longitudinally extending portions (40 and 46) slidably received in the elongated member (14).

18. The device (10) according to claim 17, wherein the device (10) further comprises at least one collar (52) securing the longitudinally extending portions (40 and 46) of the at least one loop (20) and the at least one leg (26) to one another.

19. A minimally invasive, medical device (10) for grasping, capturing, retrieving, extracting or removing stones, calculus or the like from the renal system, the device (10) comprising a reversibly collapsible basket (12) engageable with the object and an elongated member (14) for delivering the basket (12) to the location of the stones, calculus or the like; wherein the basket (12) is tipless and atraumatic, and the basket (12) comprises:

a first superelastic wire loop (20);

a second superelastic wire loop (24); and means (28) restricting relative movement of the first wire loop (20) and the second wire loop (24), the movement restricting means (28) being continuously and kinklessly formed with the first wire loop (20) and the second wire loop (24), and being positioned opposite the elongated member (14);

wherein the movement restricting means (28) comprises a first inwardly depending smaller loop (30) formed in the first wire loop (20) and a second inwardly depending smaller loop (32) formed in the second wire loop (24), interlocked with one another;

wherein the elongated member (14) comprises a flexible sheath, cannula, tube or catheter (34) of a length suitable for introduction of the basket (12) into the major and minor renal calyxes;

wherein the first wire loop (20) and the second wire loop (24) comprise longitudinally extending portions (40 and 46) slidably received in the flexible sheath, cannula, tube or catheter (34) and secured to one another; and wherein the device (10) further comprises a handle (38) connected to the flexible sheath, cannula, tube or catheter (34) and to the longitudinally extending portions (40 and 46) of the first wire loop (20) and the second wire loop (24) for withdrawing the basket (12) into the flexible sheath, cannula, tube or catheter (34) and collapsing the basket (12).

20. The device (10) according to claim 19, wherein the elongated member has an outside diameter of about 3 Fr (1 mm), and wherein the first wire loop (20) and the second wire loop (26) are composed of 0.006 in. (0.15 mm) nitinol wire.

* * * * *